(12) United States Patent
Ten Kate et al.

(10) Patent No.: US 11,204,294 B2
(45) Date of Patent: Dec. 21, 2021

(54) DEVICE AND A METHOD FOR DETERMINING WHETHER THE DEVICE IS IMMERSED IN A FLUID

(71) Applicant: KONINKLIJKE PHILIPS N.V., Eindhoven (NL)

(72) Inventors: Warner Rudolph Theophile Ten Kate, Waalre (NL); Patrick Kechichian, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 174 days.

(21) Appl. No.: 16/484,917

(22) PCT Filed: Feb. 5, 2018

(86) PCT No.: PCT/EP2018/052724
§ 371 (c)(1),
(2) Date: Aug. 9, 2019

(87) PCT Pub. No.: WO2018/146027
PCT Pub. Date: Aug. 16, 2018

(65) Prior Publication Data
US 2019/0383686 A1 Dec. 19, 2019

(30) Foreign Application Priority Data
Feb. 9, 2017 (EP) .................................... 17155325

(51) Int. Cl.
*G01L 19/00* (2006.01)
*A61B 5/11* (2006.01)
(Continued)

(52) U.S. Cl.
CPC ........ *G01L 19/0092* (2013.01); *A61B 5/1117* (2013.01); *A61B 5/1118* (2013.01);
(Continued)

(58) Field of Classification Search
CPC .... A61B 2560/0252; A61B 2560/0261; A61B 2562/0219; A61B 2562/16; A61B 5/1117;
(Continued)

(56) References Cited

U.S. PATENT DOCUMENTS 3,638,490 A * 2/1972 Buettner ................... G01F 1/00
73/861.65
3,746,472 A * 7/1973 Rupp ..................... H02K 5/132
417/9
(Continued)

FOREIGN PATENT DOCUMENTS

CN 101055666 A 10/2007
CN 103561171 A 2/2014
(Continued)

OTHER PUBLICATIONS

International Search Report dated Apr. 10, 2018.

*Primary Examiner* — Francis C Gray

(57) ABSTRACT

There is provided a device and a method of operating the device for determining whether the device is immersed in a fluid. An acceleration signal for the device is acquired (302) and a pressure within the device is detected (304). It is determined whether the device is immersed in a fluid based on a comparison of the acquired acceleration signal with the detected pressure (306).

20 Claims, 6 Drawing Sheets

(51) Int. Cl.
  *A61B 5/00* (2006.01)
  *A63B 24/00* (2006.01)
  *G05B 15/02* (2006.01)
  *G06F 1/16* (2006.01)

(52) U.S. Cl.
  CPC .......... *A61B 5/6822* (2013.01); *A61B 5/6824* (2013.01); *A63B 24/0062* (2013.01); *G01L 19/0046* (2013.01); *G05B 15/02* (2013.01); *G06F 1/1656* (2013.01); *G06F 1/1694* (2013.01); *A61B 2560/0252* (2013.01); *A61B 2560/0261* (2013.01); *A61B 2562/0219* (2013.01); *A61B 2562/16* (2013.01); *A63B 2208/03* (2013.01); *G06F 1/163* (2013.01)

(58) Field of Classification Search
  CPC ... A61B 5/1118; A61B 5/6802; A61B 5/6822; A61B 5/6824; A63B 2208/03; A63B 24/0062; G01L 19/0046; G01L 19/0092; G06F 1/163; G06F 1/1656; G06F 1/1684; G06F 1/1694; G05B 15/02
  See application file for complete search history.

(56) References Cited

U.S. PATENT DOCUMENTS

| | | | |
|---|---|---|---|
| 8,155,794 B2* | 4/2012 | Mangalam | G01M 9/06 |
| | | | 700/282 |
| 9,378,636 B2 | 6/2016 | Vallance et al. | |
| 9,612,332 B2* | 4/2017 | Wicks | G01S 7/4972 |
| 10,371,555 B2* | 8/2019 | Philipson | G01F 23/265 |
| 2014/0156216 A1 | 6/2014 | Ten Kate | |
| 2014/0230526 A1 | 8/2014 | Willemin | |
| 2014/0278220 A1 | 9/2014 | Yuen | |
| 2014/0278229 A1 | 9/2014 | Hong | |
| 2015/0025817 A1 | 1/2015 | Ten Kate | |
| 2015/0374249 A1* | 12/2015 | Elliott | A61B 5/742 |
| | | | 600/301 |
| 2016/0004283 A1 | 1/2016 | Ganguly | |
| 2017/0146644 A1* | 5/2017 | Tucker | A63B 71/0622 |

FOREIGN PATENT DOCUMENTS

| | | | | |
|---|---|---|---|---|
| CN | 204548446 U | 8/2015 | | |
| CN | 205538070 U | 8/2016 | | |
| WO | 2015113170 A1 | 8/2015 | | |
| WO | WO-2015113170 A1 * | 8/2015 | ........... | G06F 1/1626 |

* cited by examiner

DEVICE AND A METHOD FOR DETERMINING WHETHER THE DEVICE IS IMMERSED IN A FLUID

CROSS-REFERENCE TO PRIOR APPLICATIONS

This application is the U.S. National Phase application under 35 U.S.C. § 371 of International Application No. PCT/EP2018/052724, filed on Feb. 5, 2018, which claims the benefit of European Patent Application No. 17155325.8, filed on Feb. 9, 2017. These applications are hereby incorporated by reference in their entirety herein.

TECHNICAL FIELD OF THE INVENTION

The invention relates to the field of devices and, in particular, wearable devices and methods for determining whether the device is immersed in a fluid.

BACKGROUND TO THE INVENTION

There are many situations in which a device may be immersed in a fluid. For example, this is often the case in healthcare monitoring applications. Accelerometers are widely used in these applications and a common wearing location for an accelerometer is on the wrist, where the accelerometer can be housed in a watch-like device. A typical healthcare monitoring application includes activity monitoring, which can be used to estimate energy expenditure or fitness. For example, by measuring the number of steps the wearer of the device takes over the day, the device can keep track of whether the wearer is walking sufficiently. A particular group of activities that may be monitored are sports that involve water, such as rowing and swimming. Another example of a healthcare monitoring application includes monitoring people during rehabilitation and monitoring the elderly, where it is preferable to wear the device during bathing. Thus, there exist situations in which it may be necessary for a device to be worn in water.

However, the immersion of a device in a fluid (such as water) can damage the device, especially the electronic components and other internal components of the device. This implies that the device needs to be sealed to prevent fluid entering the device and to thus protect the internal components against fluid. However, this is not always ideal and can prove to be disadvantageous in certain situations. For example, in many applications, the addition of an air pressure sensor can improve the accuracy of a monitoring function of a device and this requires the device to have a vent that allows outside pressure to pass into the device to reach the air pressure sensor. An air pressure sensor may be beneficial, for example, in more accurately distinguishing regular level walking from walking up and/or down stairs, in detecting rising from a chair or bed, in fall detection (which requires accurate height change information), and in depth estimation while swimming. Air pressure sensors are also used to measure altitude in mountainous regions, which can be particularly valuable for people with respiration and cardiac conditions.

A drawback with a device comprising an air pressure sensor is that the need to have a vent to allow outside pressure into the device directly conflicts with the need to seal the device in case the device is immersed in a fluid. An existing approach to resolve this issue is to protect the internal components of non-waterproof devices against outside fluid by covering the vent with a material that is air-permeable but also water-repellent. An example of a typical material used in such an approach is GORE-TEX®. However, while these materials are water-repellent, the materials are not able to protect the internal components when the device is immersed in a fluid for a sustained duration since the materials are not waterproof. For example, a number of materials are rated to a certain depth for a specific duration (such as 1 m for 30 minutes under an ingress protection rating IPX7). It is therefore important to be able to determine whether the device is immersed in a fluid such that appropriate action may be taken to protect the device.

In this respect, US 2016/0004283 discloses a portable electronic device that includes submersion detection circuitry for detecting when the electronic device is submerged in water. Specifically, when a pressure sensor in the submersion detection circuitry detects a sharp increase in pressure, the submersion detection circuitry determines that the electronic device is submerged in water and takes appropriate action (for example, powering down electrical components in the electronic device). However, this method can be unreliable as there are certain situations in which the device can fail to detect that it is submerged. For example, one situation is where the user of the device is swimming in water. In this situation, there is no change in average height of the device in the water and thus no sharp increase in pressure. Instead, only random fluctuations in pressure are detected and thus no determination that the device is submerged is made. Moreover, in order to detect a sharp increase in pressure, it is necessary for the submersion detection circuitry to measure the pressure continuously to ensure that the circuitry is on when the sharp pressure increase occurs, since it is not possible to know in advance the moment that this will occur. Therefore, the disclosed method is unreliable or energy inefficient. Also, in order to measure the (sharp increase in) pressure, the pressure sensor needs to be vented to outside the housing in which it is contained.

There is thus a need for an improved device and method for determining whether the device is immersed in a fluid.

SUMMARY OF THE INVENTION

As noted above, the limitation with existing approaches for determining whether a device is immersed in fluid is that the approaches are often unreliable and can also be energy inefficient where it is necessary to monitor pressure continuously. It would thus be valuable to have an improved device and method for determining whether the device is immersed in a fluid, which overcomes the existing problems.

Therefore, according to a first aspect of the invention, there is provided a method for determining whether a device is immersed in a fluid. The method comprises acquiring an acceleration signal for the device, detecting a pressure within the device, and determining whether the device is immersed in a fluid based on a comparison of the acquired acceleration signal with the detected pressure.

In some embodiments, there is provided a method for determining whether a device is immersed in a fluid. The method comprises acquiring an acceleration signal for the device, detecting a pressure within the device, and determining whether the device is immersed in a fluid based on a comparison of a first value determined based on the acquired acceleration signal with a second value determined based on the detected pressure. As disclosed in the different embodiments below, the first value and the second value may refer to (i) a change in height for the device determined from the acquired acceleration signal over a predefined time period, and a change in pressure determined from the pressure detected within the device over the predefined time period, respectively; (ii) a change in pressure determined from the change in height determined from the acquired acceleration signal, and a change in pressure determined from the pressure detected within the device, respectively; (iii) a first velocity of the device determined based on the determined change in height over the predefined time period, and a second velocity of the device determined based on the detected change in pressure over the predefined time period, respectively.

In some embodiments, the method may further comprise determining a change in height for the device from the acquired acceleration signal over a predefined time period, detecting a change in pressure from the pressure detected within the device over the predefined time period, and determining whether the device is immersed in the fluid may be based on a comparison of the determined change in height with the detected change in pressure.

In some embodiments, determining whether the device is immersed in the fluid may comprise determining a ratio of the determined change in height to the detected change in pressure and identifying the fluid in which the device is immersed based on the determined ratio.

In some embodiments, the method may further comprise determining a change in pressure from the change in height determined from the acquired acceleration signal and determining whether the device is immersed in the fluid may be based on a comparison of the determined change in pressure with the detected change in pressure.

In some embodiments, the device may be determined to be not immersed in the fluid when the determined change in pressure and the detected change in pressure are equal or differ by less than a threshold and the device may be determined to be immersed in the fluid when the determined change in pressure and the detected change in pressure differ by more than the threshold.

In some embodiments, the method may further comprise determining a first velocity of the device based on the determined change in height over the predefined time period, determining a second velocity of the device based on the detected change in pressure over the predefined time period, and determining whether the device is immersed in the fluid may be based on a comparison of the determined first velocity with the determined second velocity.

In some embodiments, the method may further comprise determining a ratio of the change in height to the time period over which the height change occurs to acquire a vertical velocity of the device and comparing the acquired vertical velocity with a threshold to determine whether the detected change in pressure is reliable.

In some embodiments, the method may further comprise allowing a valve of the device to open when the device is determined to be not immersed in the fluid and prohibiting opening of the valve when the device is determined to be immersed in the fluid. In some embodiments, the method may further comprise, where the valve is allowed to open, closing the valve once the pressure within the device is equalised with a pressure outside the device.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to a third aspect of the invention, there is provided a device comprising an accelerometer configured to acquire an acceleration signal for the device, a pressure sensor configured to detect a pressure within the device, and a processor configured to determine whether the device is immersed in the fluid based on a comparison of the acquired acceleration signal with the detected pressure.

In some embodiments, the device may further comprise a pressure chamber housing the pressure sensor, wherein the pressure chamber may have a volume that is less than a maximum volume.

In some embodiments, the device may further comprise a valve to allow fluid to enter the device when the valve is open, wherein the processor may be configured to allow the valve to open when the device is determined to be not immersed in the fluid and prohibit opening of the valve when the device is determined to be immersed in the fluid.

In some embodiments, the device may further comprise one or more apertures, wherein the one or more apertures may be covered by a flexible and impermeable membrane. In some embodiments, the pressure sensor may be positioned less than a maximum distance from at least one of the one or more other apertures.

According to the aspects and embodiments described above, the limitations of existing techniques are addressed. In particular, according to the above-described aspects and embodiments, a more reliable determination of whether the device is immersed in a fluid can be achieved by basing the determination on a comparison of two sensing modalities, namely by comparing parameters based on the acquired acceleration signal and parameters based on the detected pressure. Moreover, according to the above-described aspects and embodiments, the method does not need to be run continuously and thus power can be conserved. In particular, the method can be employed at any instant in time to reliably determine whether the device is immersed in a fluid at that time instant.

In this way, there is provided a more reliable and energy efficient detection mechanism to decide whether a device is outside or immersed in a fluid (for example, water). This enables the inclusion of an air pressure sensor in the device while at the same time the device can remain sealed against the fluid.

There is thus provided an improved device and method for determining whether the device is immersed in a fluid, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides a device and method for determining whether the device is immersed in a fluid, which overcomes the existing problems.

In some embodiments, the device can be a wearable device. A wearable device may be any device that is configured to be worn by a user. For example, a wearable device may be a device configured to be worn on or around the neck of the user, the wrist of the user, the waist of the user, the back of the user, the chest of the user, or any other part of the user. In a neck-worn embodiment, the device can be in the form of a pendant that is worn on a cord, chain, necklace, or collar around the neck of the user. In a wrist-worn embodiment, the device may be provided in the form of a wrist band, a wrist strap, or a wrist watch. The device may be shaped appropriately for the purpose.

In some embodiments, the device can be a certain type of device or a device with a dedicated function. For example, the device may be a health monitoring device. A health monitoring device can be configured to monitor physiological characteristics, behavioural characteristics and/or movements of a user of the device for the purpose of monitoring the health of the user. Alternatively or in addition, the device may be an activity monitoring device. An activity monitoring device can be configured to monitor physiological characteristics, behavioural characteristics and/or movements of a user of the device during activities such as walking (for example, pedometers) including regular level walking and stair walking, swimming, biking, sitting, sleeping, or general daily activities, and may be used to detect the occurrence of specific events such as the user falling, to detect the risk of a fall, to detect quality of movement, to detect energy expenditure, or similar.

Figure 1:
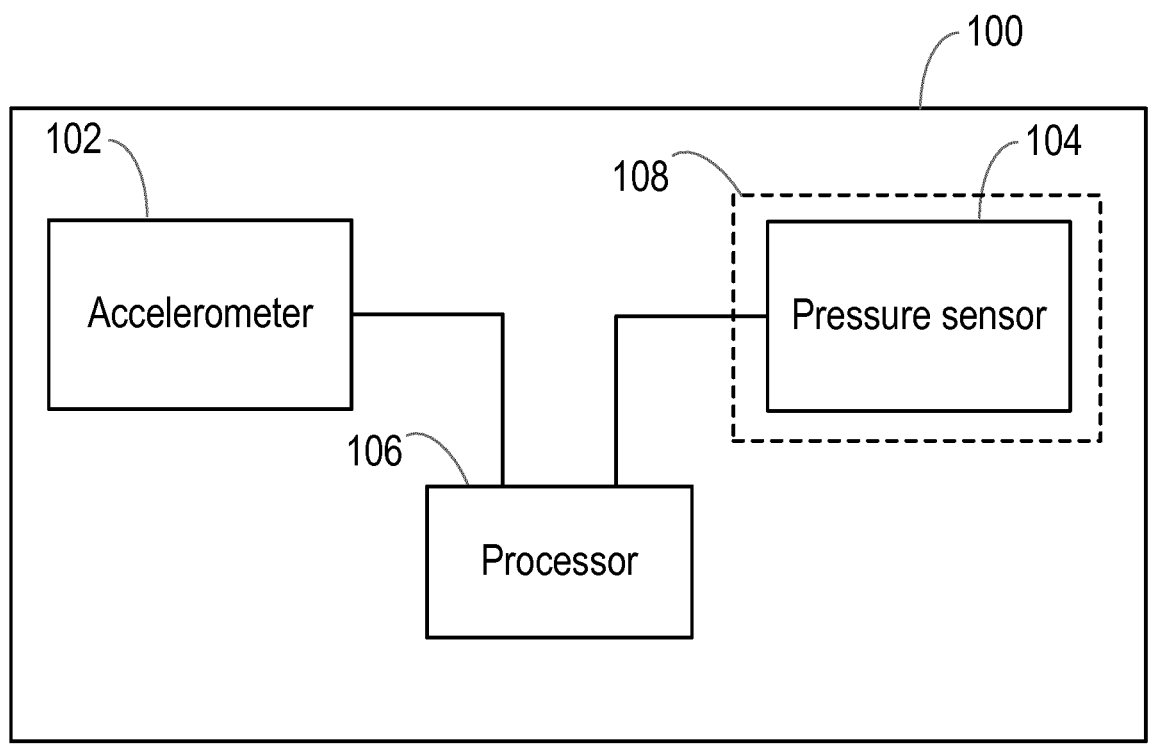
FIG. 1 is a block diagram of a device according to an embodiment.

FIG. 1 illustrates an example of the device 100 according to an embodiment. With reference to FIG. 1, the device 100 comprises an accelerometer 102 configured to acquire an acceleration signal for the device 100 and a pressure sensor 104 configured to detect a pressure within the device 100. As illustrated in FIG. 1, in any of the embodiments described herein, the device 100 can optionally comprise a pressure chamber 108 housing the pressure sensor 104. In some embodiments, the pressure chamber 108 may be a rigid (or non-flexible) wall inside the device 100, which is positioned against the internal rim of the device 100. The pressure chamber 108 may have a volume that is less than a maximum volume. In some embodiments, this maximum volume may be of the order of a cubic millimetre or smaller (for example, compared a device 100 with a volume of the order of a cubic centimetre). In some embodiments, the pressure chamber 108 can be a rigid chamber.

In some embodiments, the device 100 may further comprise a temperature sensor. For example, a sensitivity and reading offset of the pressure sensor 104 can change with temperature and thus a temperature sensor may be used to compensate for such changes due to temperature. In this way, more accurate pressure measurements can be acquired. In some embodiments, the pressure sensor 104 itself may comprise the temperature sensor. In other embodiments, the temperature sensor may be a separate sensor to the pressure sensor 104.

The device 100 also comprises a processor 106 configured to determine whether the device 100 is immersed in a fluid based on a comparison of the acquired acceleration signal with the detected pressure. Although not illustrated, in some embodiments, the apparatus 100 may also comprise a memory configured to store program code that can be executed by the processor 106 to perform the method described herein. The memory can be used to store information, data, signals and measurements acquired or made by the processor 106 of the device 100.

In some embodiments, the device 100 may comprise a flexible housing that houses or holds the accelerometer 102, the pressure sensor 104, the processor 106, and optionally any other internal (for example, electronic) components of the device 100. The pressure sensor 104 may be configured to detect pressure changes within the device 100 that occur from the flexible housing deforming due to a difference between the internal pressure of the device 100 and the external pressure on the device 100. For example, an increase of external pressure on the device 100 can cause the internal volume of the device 100 to decrease and thus the internal pressure of the device 100 to increase. Likewise, a decrease of external pressure on the device 100 can cause the internal volume of the device 100 to increase and thus the internal pressure of the device to decrease.

Alternatively or in addition to the flexible housing, in some embodiments, the device 100 may comprise one or more apertures, where each aperture is covered by a flexible and impermeable membrane. The size of an aperture can vary and, in some embodiments, may typically range from a fraction of a square millimetre to a few square millimetres. An impermeable membrane is a membrane that does not allow fluid to pass through the aperture that the membrane covers. In effect, a membrane seals the aperture that it covers. In one example, a membrane may be composed of a water-impermeable material such as a thin plastic (for example, polyurethane). A membrane is flexible such that the pressure changes outside the device 100 can pass into the device 100 to be detected by the pressure sensor 104. Thus, in these embodiments, the pressure sensor 104 may be configured to detect pressure changes within the device 100 that occur from the flexible membrane deforming due to a difference between the internal pressure of the device 100 and the external pressure on the device 100 (which can be caused in the manner described earlier with reference to the flexible housing). In some embodiments comprising one or more apertures, where each aperture is covered by a flexible and impermeable membrane, the housing of the device 100 may be rigid instead of flexible or have a level of flexibility somewhere in between. In some embodiments, the level of flexibility of the housing of the device 100 can vary.

Figure 2A:
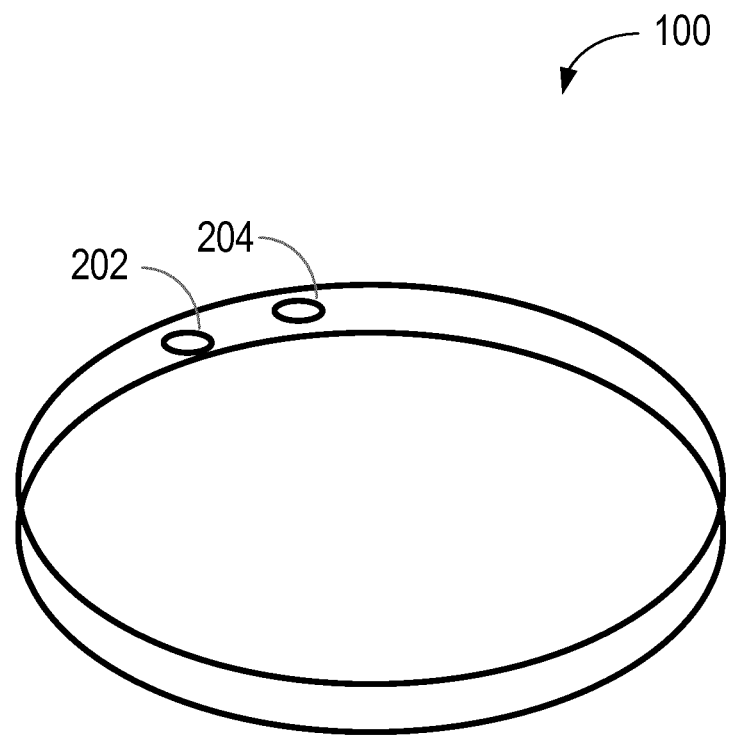
FIGS. 2A and 2B are block diagrams of the device according to an embodiment.
Figure 2B:
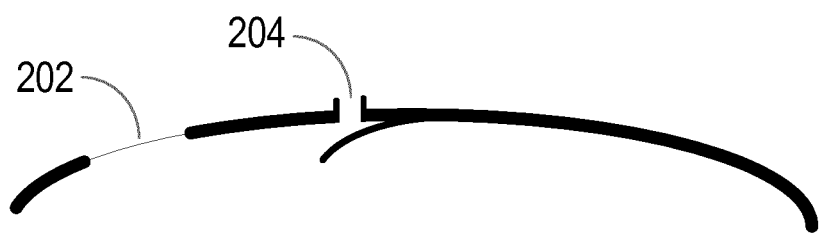

FIGS. 2A and 2B illustrate an example of the device 100 according to an embodiment. FIG. 2B is an enlarged, cut-away, view from above of the side of the device 100 illustrated in FIG. 2A. Although not shown in FIGS. 2A and 2B, as described above with reference to FIG. 1, the device 100 comprises the accelerometer 102, the pressure sensor 104, the processor 106 and, optionally, the pressure chamber 108.

In the example embodiment illustrated in FIGS. 2A and 2B, the device 100 also comprises an aperture 202. The aperture 202 is provided in the side rim of the device 100. Although only a single aperture is illustrated in this example embodiment, it will be understood that the device 100 may comprise one or more apertures 202 (i.e. a single aperture or multiple apertures), as mentioned earlier. The aperture 202 of the device 100 is covered by a flexible and impermeable membrane.

Although not illustrated in FIGS. 2A and 2B, in some embodiments, the pressure sensor 104 of the device 100 may be positioned less than a maximum distance from (for example, close to) at least one of the one or more other apertures 202 and thus also from the flexible membrane covering the at least one aperture 202. As mentioned earlier, the pressure sensor 104 may be housed in a rigid (or flexible) pressure chamber 108. The pressure chamber 108 has a volume that is less than the volume of the full housing of the device 100. This allows the at least one aperture 202 to be smaller and the flexible membrane covering the at least one aperture 202 to be less flexible. The pressure chamber 108 encloses the flexible membrane and thus the aperture 202.

In this way, by mounting the pressure sensor 104 close to the flexible membrane and enclosing the pressure sensor 104 and flexible membrane in a rigid (or flexible) pressure chamber 108, the volume inside the pressure chamber 108 can be small such that a pressure change requires only a small deformation (for example, bending) of the membrane. According to Boyle's law:

$$P \cdot V = (P+dP) \cdot (V-dV), \quad (1)$$

where P is the pressure, V is the volume, dP is the change (specifically, the increment) in the pressure and dV is the change (specifically, the decrement) in volume. Assuming an air pressure of 1013 hPa at a temperature of 25° C. at sea level, the pressure increase under 1 m of water can be calculated from Equation (1) as 98 hPa, which is approximately a 10% pressure increment. Therefore, for a 10% pressure increment (which corresponds to roughly a depth of 1 m in water), the volume in the pressure chamber 108 has to shrink by 10%. For a cavity of 1 cm$^3$, assuming a square membrane of 1 cm$^2$, the membrane has to bend 1 mm inside, which is a feasible distance, resulting in a smaller volume of 0.9 cm$^3$.

As illustrated in FIGS. 2A and 2B, the device 100 may further comprise a valve 204. The valve 204 is provided in the side rim of the device 100. In embodiments where the device 100 comprises a pressure chamber 108, the valve 204 may be connected to the pressure chamber 108, so as to equalise the pressure in the pressure chamber 108 with the outside pressure. The valve 204 is a switchable valve in that the valve 204 can be switched between an open state and a closed state. In one example embodiment, a mechanism for opening and closing the valve 204 can comprise a spring that is biased toward the closed state and a magnetic coil that is controllable to pull the spring to the open state. In another example embodiment, an electroactive polymer and ionic electroactive polymer can be used to create a cantilever that bends to open and close the valve 204. However, it will be appreciated that these are only some examples and other mechanisms may alternatively be employed to operate the switching of the valve 204. The valve 204 allows fluid to enter the device 100 when the valve 204 is open. The opening of the valve 204 enables the internal pressure of the device 100 to change with outside pressure. In this way, the pressure of the device 100 can be equalised with the pressure outside the device 100. In embodiments where the device 100 comprises a pressure chamber 108, the pressure chamber 108 may enclose the valve 204 (for example, in addition to enclosing the aperture 202, as mentioned earlier).

In embodiments where the device 100 comprises a valve 204, the processor 106 of the device 100 can be configured to allow the valve 204 to open when the device 100 is determined to be not immersed in a fluid such as a liquid (for example, water or any other liquid) and prohibit opening of the valve 204 when the device 100 is determined to be immersed in that fluid. In a similar manner, the processor 106 of the device 100 can be configured to allow the valve 204 to open when the device 100 is determined to be immersed in a fluid such as a gas (for example, air or any other gas). Thus, while a flexible housing of the device 100 and/or one or more flexible membranes, each covering an aperture 202 of the device 100, enable an internal pressure of the device 100 to change with an external pressure on the device 100, the valve 204 of the device 100 can be controlled to shift or to equalise this pressure. In some embodiments, the valve 204 may be covered by an air-permeable and water-repellent membrane (such as GORE-TEX® or any other air permeable membrane). In this way, when the valve 204 is open, the pressure in the device 100 can be equalised with the pressure outside the device 100, whilst at the same time pollution and moisture can be prevented from entering the device 100.

In an embodiment where the device 100 does not comprise a valve 204, the flexible membrane covering the aperture 202 may be flexible enough (for example, have a low enough stiffness) to pass the range of outside pressures into the device 100 to be detected by the pressure sensor 104. Alternatively or in addition, as described above, the pressure sensor 104 may be housed in a pressure chamber 108 that has a volume that is less than a maximum volume (i.e. that has a small volume). In some embodiments, the maximum volume may be a value set based on the characteristics (for example, the flexibility) of the membrane covering the aperture 202 or a value that is determined by the constraints set by Equation (1). Again, due to Boyle's law, a pressure chamber 108 with a small volume reduces the excursion needed by the membrane to equalise the pressure inside the device 100 with the outside pressure.

Although not illustrated in FIGS. 1, 2A and 2B, in any of the embodiments described herein, the device 100 may also comprise a user interface configured to provide information, data, or signals to the user of the device 100. The user interface may, alternatively or in addition, be configured to enable the user of the device 100 to provide a user input, interact with and/or control the device 100. Thus, the user interface of the device 100 may be any user interface that enables information, data, or signals to be provided to the user of the device 100 and, optionally or in addition, that enables the user of the device 100 to provide a user input, interact with and/or control the device 100. For example, the user interface may comprise one or more buttons, a keypad, a touch screen, an application (for example, on a smart device such as a smart watch), a display screen, a graphical user interface (GUI) or any other visual component, one or more speakers, one or more microphones or any other audio component, one or more lights, a component for providing tactile feedback (such as a vibration function), or any other user interface components, or any combination of user interface components. In one example embodiment of the device 100, the top surface of the device 100 (or the housing of the device 100) can comprise a display.

It will be appreciated that FIGS. 1, 2A and 2B only show the components required to illustrate an aspect of the invention and, in a practical implementation, the device 100 may comprise additional components to those shown. For example, in any of the embodiments described herein, the device 100 may comprise a communications interface (or circuitry) for enabling the device 100 to communicate with other devices, either wirelessly or via a wired connection. In any of the embodiments described herein, the device 100 may comprise a battery or other power supply for powering the device 100 or means for connecting the device 100 to a mains power supply.

Although various examples of the form that the device 100 may take have been provided above, it will be appreciated that the device 100 is not limited to these forms and that other forms for the device 100 are also possible.

Figure 3:
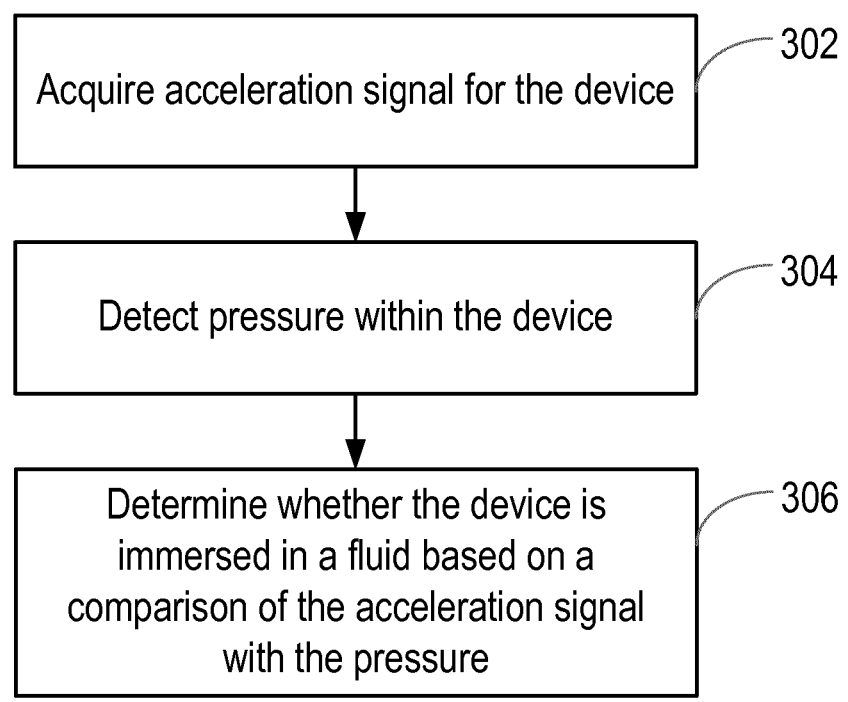
FIG. 3 is a flow chart illustrating a method according to an embodiment.

FIG. 3 illustrates a method 300 for determining whether a device 100 is immersed in a fluid according to an embodiment. The illustrated method 300 can generally be performed by or under the control of the processor 106 of the device 100.

At block 302 of FIG. 3, an acceleration signal is acquired for the device 100. The accelerometer 102 of the device 100 is configured to acquire the acceleration signal.

For example, the processor 106 of the device 100 may be configured to control the accelerometer 102 to acquire the acceleration signal. At block 304 of FIG. 3, a pressure within the device 100 is detected. The pressure sensor 104 of the device 100 is configured to detect the pressure within the device 100. For example, the processor 106 of the device 100 may be configured to control the pressure sensor 104 to detect the pressure. At block 306 of FIG. 3, it is determined whether the device is immersed in a fluid based on a comparison of the acquired acceleration signal with the detected pressure. In particular, the processor 106 of the device is configured to determine whether the device is immersed in a fluid based on the comparison. The comparison of the acquired acceleration signal with the detected pressure can be implemented in a manner of different ways and some example embodiments will now be described with reference to FIGS. 4, 5 and 6. However, these examples are to be considered in no way limiting.

Figure 4:
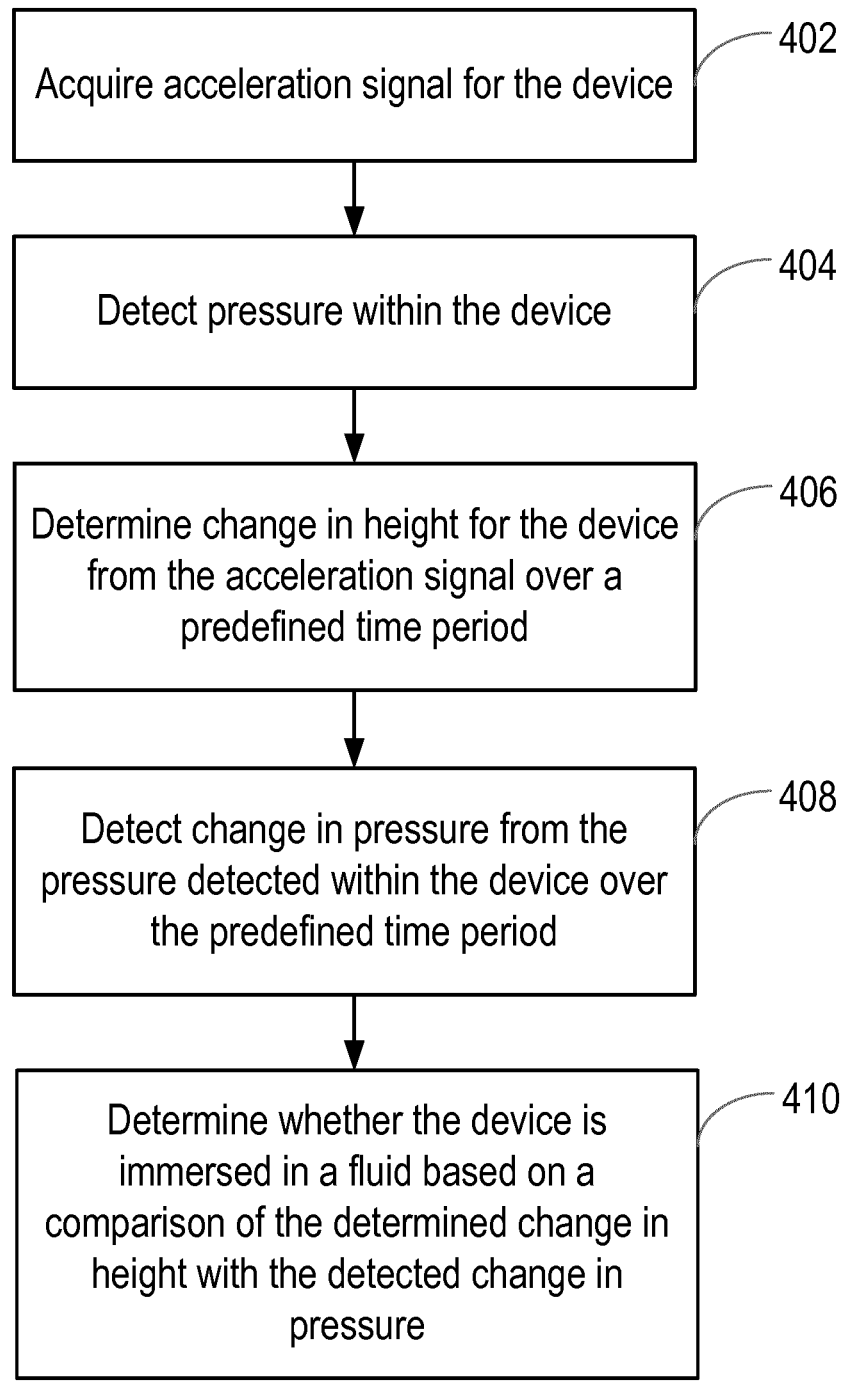
FIG. 4 is a flow chart illustrating a method according to an example embodiment.

FIG. 4 illustrates a method 400 for determining whether a device 100 is immersed in a fluid according to an example embodiment. The illustrated method 400 can generally be performed by or under the control of the processor 106 of the device 100.

At block 402 of FIG. 4, an acceleration signal is acquired for the device 100. The accelerometer 102 of the device 100 is configured to acquire the acceleration signal. For example, the processor 106 of the device 100 may be configured to control the accelerometer 102 to acquire the acceleration signal. At block 404 of FIG. 4, a pressure within the device 100 is detected. The pressure sensor 104 of the device 100 is configured to detect the pressure within the device 100. For example, the processor 106 of the device 100 may be configured to control the pressure sensor 104 to detect the pressure.

At block 406 of FIG. 4, a change in height for the device 100 is determined from the acquired acceleration signal over a predefined time period. Thus, the acceleration signal acquired from the accelerometer 102 can be used to determine the change in height for the device 100. The change in height for the device 100 may be determined from the acceleration signal using any of the standard techniques that will be known to the skilled person. For example, in one embodiment, the height change determination can comprise determining an acceleration component in a vertical direction from the acquired acceleration signal, removing gravity from the determined vertical acceleration component and computing a double integral of the determined vertical acceleration component with gravity removed to determine the change in height for the device 100. In this embodiment, it may be assumed that the initial (vertical) velocity of the device 100 is zero.

At block 408 of FIG. 4, a change in pressure is detected from the pressure detected within the device 100 over the predefined time period. This change in pressure may be due to a deformation (for example, bending) of a flexible housing of the device 100, a deformation (for example, bending) of one or more flexible membranes each covering an aperture 202 of the device 100, or a deformation of both a flexible housing and one or more flexible membranes of the device 100 (as described earlier).

At block 410 of FIG. 4, it is determined whether the device 100 is immersed in a fluid based on a comparison of the determined change in height with the detected change in pressure. Thus, in other words, the height change determined from the acceleration signal of the accelerometer 102 is compared to the pressure change detected from the pressure sensor 104 over the same time period to determine whether the device 100 is immersed in a fluid. The processor 106 of the device 100 is configured to determine whether the device 100 is immersed in a fluid based on the comparison.

In some embodiments, the determination of whether the device 100 is immersed in a fluid can comprise determining a ratio of the determined change in height to the detected change in pressure and identifying the fluid (for example, air, water, or any other fluid) in which the device 100 is immersed based on the determined ratio. For example, the pressure change for a given height change in water is much larger than in air. Specifically, in water, a height change of 1 m corresponds to a pressure change of approximately 100 hPa (at water surface) compared to a height change of 1 m corresponding to a pressure change of approximately 12.5 Pa in air (at sea level). Thus, the comparison of the change in height determined from the acceleration signal acquired by the accelerometer 102 with the change in pressure detected from the pressure detected by the pressure sensor 104 can provide a decision criterion to distinguish whether the device 100 is outside or immersed in water.

In some embodiments, the identification of the fluid in which the device 100 is immersed can take into account mass density. In general, a mass density of a liquid is larger than a mass density of a gas and hence the ratio of the determined change in height to the detected change in pressure is larger when the device 100 is immersed in a liquid than when the device 100 is immersed in a gas. Thus, it is possible to distinguish between two or more fluids having different mass densities. This is possible through the following equation:

$$dP = -\rho \cdot g \cdot dH, \quad (2)$$

where dP is the detected change in pressure, $\rho$ is the mass density, g is gravity, and dH is the determined change in height, where an upward change in height is a positive value and a downward change in height is a negative value. Thus, according to Equation (2), the pressure increases when the height decreases. In some embodiments, it may be assumed that gravity equals 9.81 ms$^{-2}$ at sea level. In alternative embodiments, the value for gravity may be determined from the accelerometer 102 as the acceleration value when the device 100 is stationary (for example, not accelerating or free falling) or the mean or median (or any other estimator for determining a central value) of the acceleration value when the device 100 is moving. In these alternative embodiments, the detected change in pressure dP and the determined change in height dH may be adapted based on the current value for gravity determined from the accelerometer 102.

For small pressure changes (where small is relative to the absolute pressure), the change in the pressure dP within the device 100 is related to the height change dH of the device 100 as follows:

$$dP = -\gamma \cdot P \cdot dH \quad (3)$$

where γ is a constant that depends on one or more properties of the surrounding fluid in which the device 100 is immersed. For example, the constant γ may depend one or more of the (molecular) mass of the surrounding fluid in which the device 100 is immersed and the temperature of the surrounding fluid in which the device 100 is immersed. In air at sea level (where pressure P is approximately equal to 1000 hPa) and at room temperature, the constant γ is approximately equal to $1.19 \times 10^{-4}$ m$^{-1}$, and γP is approximately equal to 12 Pa/m. In water, at the surface, γP is approximately equal to 100 hPa/m. Thus, the constant γ is approximately 1000 times larger in water than it is in air. In this way, by comparing the change in height dH of the device 100 determined from one sensor (specifically, the accelerometer 102) with the change in pressure dP within the device 100 detected from the other sensor (specifically, the pressure sensor 104), it is possible to test whether the constant γ matches that of air or water.

Figure 5:
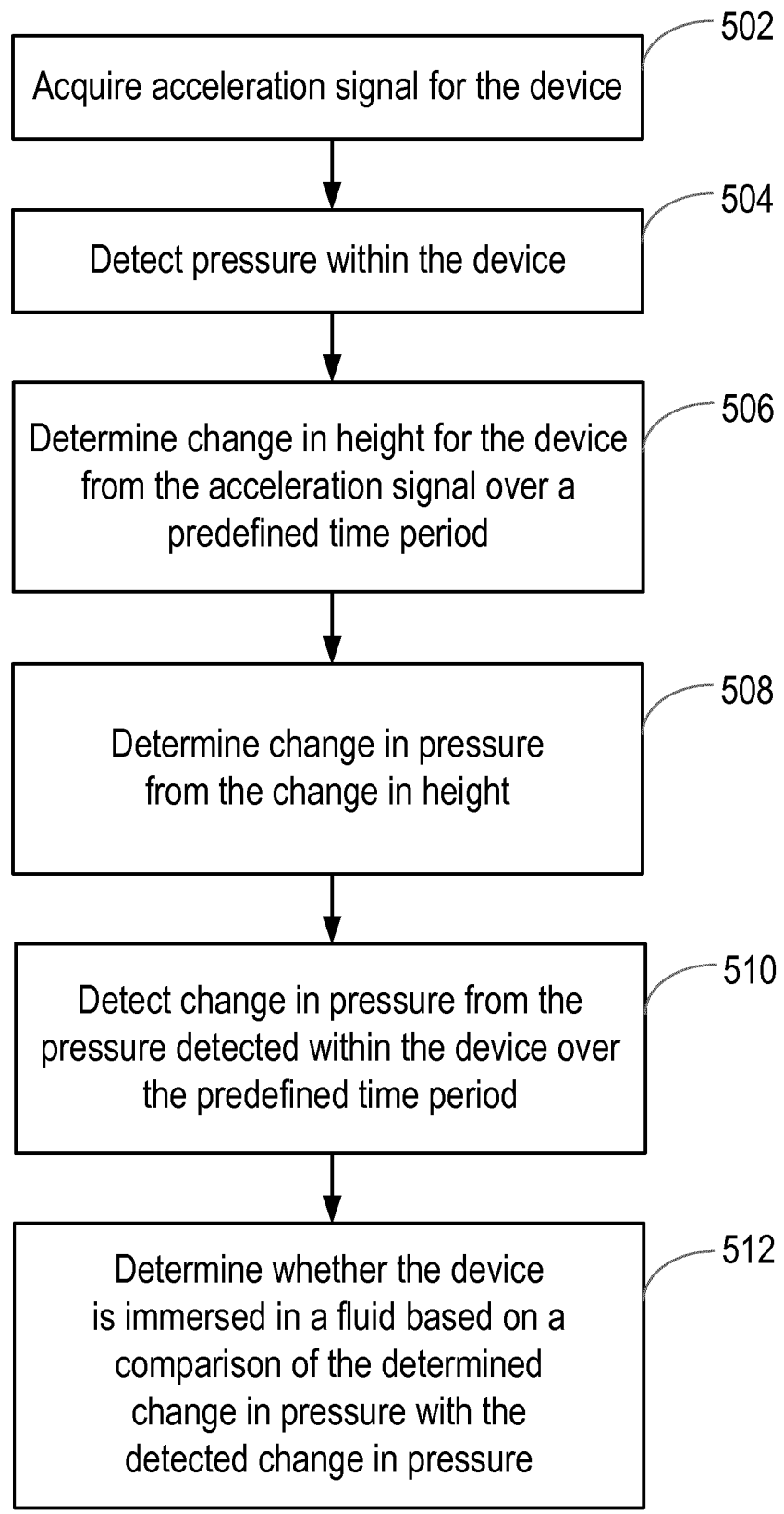
FIG. 5 is a flow chart illustrating a method according to another example embodiment.

FIG. 5 illustrates a method 500 for determining whether a device 100 is immersed in a fluid according to an example embodiment. The illustrated method 500 can generally be performed by or under the control of the processor 106 of the device 100.

At block 502 of FIG. 5, an acceleration signal is acquired for the device 100. The accelerometer 102 of the device 100 is configured to acquire the acceleration signal. For example, the processor 106 of the device 100 may be configured to control the accelerometer 102 to acquire the acceleration signal. At block 504 of FIG. 5, a pressure within the device 100 is detected. The pressure sensor 104 of the device 100 is configured to detect the pressure within the device 100. For example, the processor 106 of the device 100 may be configured to control the pressure sensor 104 to detect the pressure.

At block 506 of FIG. 5, a change in height for the device 100 is determined from the acquired acceleration signal over a predefined time period. In other words, block 406 of FIG. 4 is performed and the corresponding description will be understood to apply but will not be repeated here. At block 508 of FIG. 5, a change in pressure is determined from the change in height determined from the acquired acceleration signal. For example, in some embodiments, the change in pressure may be determined from the change in height according to Equation (3) above. Thus, an equivalent pressure change can be computed from the height change. At block 510 of FIG. 5, a change in pressure is detected from the pressure detected within the device 100 over the predefined time period. In other words, block 408 of FIG. 4 is performed and the corresponding description will be understood to apply but will not be repeated here.

At block 512 of FIG. 5, it is determined whether the device 100 is immersed in a fluid based on a comparison of the determined change in pressure with the detected change in pressure. In other words, the pressure change computed from the height change is compared to the pressure change measured by the pressure sensor 104. In some embodiments, the device 100 may be determined to be not immersed in a fluid such as a liquid (for example, water or any other liquid) when the determined change in pressure and the detected change in pressure are equal or differ by less than a threshold. This may be, for example, when the changes in pressure are comparable in size or comparable in order. The threshold can be adaptable, for example, based on an estimate of the accuracy (or variance) of the determined height changes. In some embodiments, the threshold may be at least 1% of the pressure change measured by the pressure sensor 104. In other embodiments, the threshold may be higher and may, for example, be at least 2%, at least 5% or at least 10% of the pressure change measured by the pressure sensor 104.

In some embodiments, the device 100 may be determined to be immersed in a fluid such as a liquid (for example, water or any other liquid) when the determined change in pressure and the detected change in pressure differ by more than the threshold. In a similar manner, in some embodiments, the device 100 may be determined to be immersed in a fluid such as a gas (for example, air or any other gas) when the determined change in pressure and the detected change in pressure are equal or differ by less than the threshold.

Figure 6:
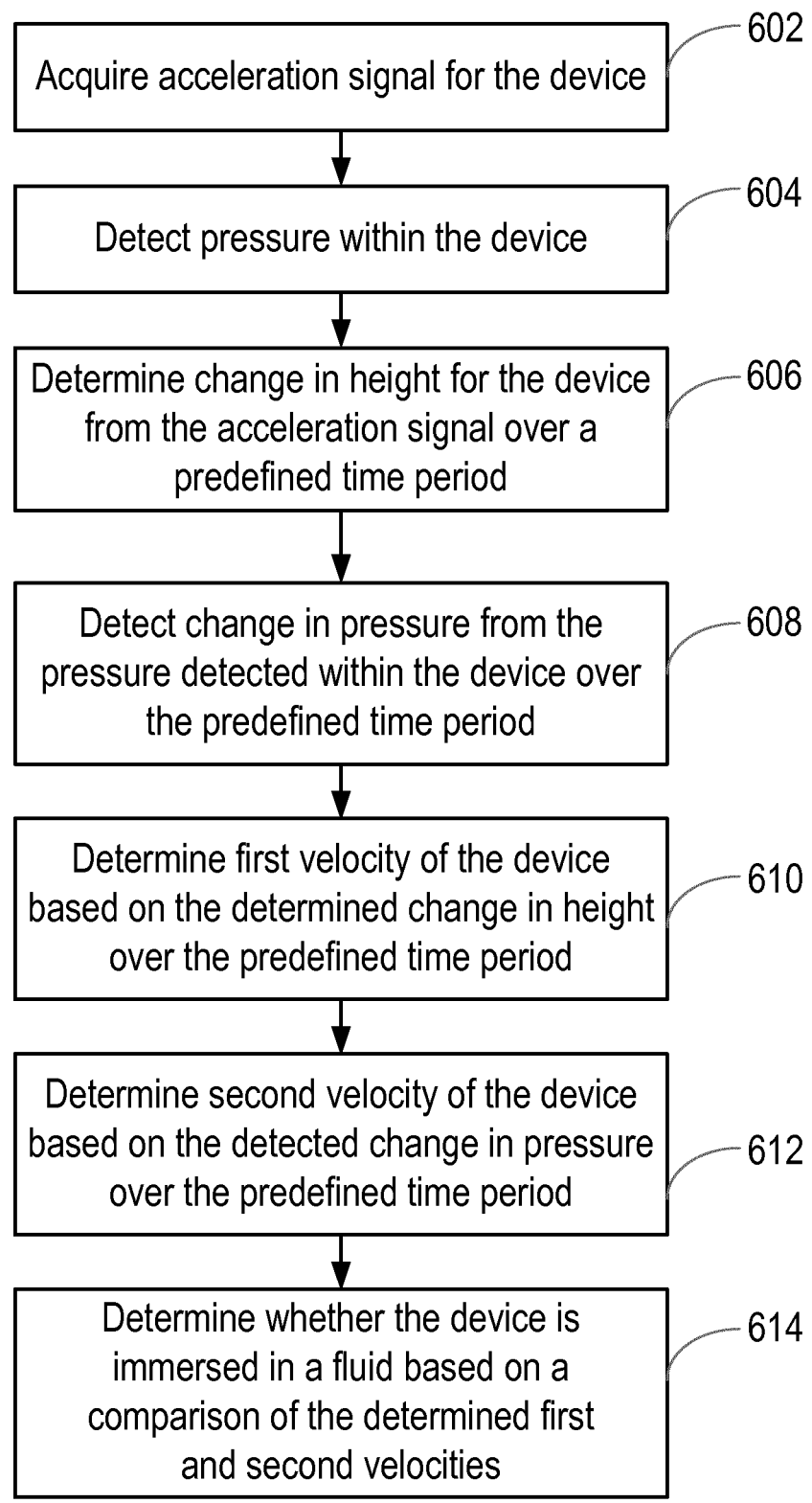
FIG. 6 is a flow chart illustrating a method according to another example embodiment.

FIG. 6 illustrates a method 600 for determining whether a device 100 is immersed in a fluid according to an example embodiment. The illustrated method 600 can generally be performed by or under the control of the processor 106 of the device 100.

At block 602 of FIG. 6, an acceleration signal is acquired for the device 100. The accelerometer 102 of the device 100 is configured to acquire the acceleration signal. For example, the processor 106 of the device 100 may be configured to control the accelerometer 102 to acquire the acceleration signal. At block 604 of FIG. 6, a pressure within the device 100 is detected. The pressure sensor 104 of the device 100 is configured to detect the pressure within the device 100. For example, the processor 106 of the device 100 may be configured to control the pressure sensor 104 to detect the pressure.

At block 606 of FIG. 6, a change in height for the device 100 is determined from the acquired acceleration signal over a predefined time period. In other words, block 406 of FIG. 4 (or block 506 of FIG. 5) is performed and the corresponding description will be understood to apply but will not be repeated here. At block 608 of FIG. 6, a change in pressure is detected from the pressure detected within the device 100 over the predefined time period. In other words, block 408 of FIG. 4 (or block 510 of FIG. 5) is performed and the corresponding description will be understood to apply but will not be repeated here.

At block 610 of FIG. 6, a first velocity of the device 100 is determined based on the determined change in height over the predefined time period. For example, the first velocity of the device 100 may be determined by dividing the determined change in height by the predefined time period to obtain an average velocity. Alternatively, the first velocity of the device 100 may be determined by integrating the acceleration signal over time to obtain an instantaneous velocity (at the time where the integration stops). The integration may be started where there is no movement and it can be assumed that velocity is zero. In this way, a first velocity of the device 100 may be determined from the acceleration signal acquired from the accelerometer 102.

At block 612 of FIG. 6, a second velocity of the device 100 is determined based on the detected change in pressure over the predefined time period. For example, the detected change in pressure is converted into a change in height using Equation (3) and the second velocity of the device 100 is determined from this change in height. For example, the second velocity may be determined by dividing the change in height by the predefined time period to obtain an average velocity. Alternatively, the second velocity may be determined by differentiating the height change with respect to time to obtain an instantaneous velocity (at the time where the differentiation stops). In this way, a second velocity of the device 100 may be determined from the pressure change detected by the pressure sensor 104.

At block 614 of FIG. 6, it is determined whether the device 100 is immersed in a fluid based on a comparison of the determined first velocity with the determined second velocity. In an embodiment where the first and second velocities are average velocities, the two average velocities are compared. In an embodiment where the first and second velocities are instantaneous velocities, a time series of the instantaneous velocities are compared. In another embodiment where the first and second velocities are instantaneous velocities, a time series of the instantaneous velocities for each is first averaged and the averages of the time series of the instantaneous velocities is compared. A time series of instantaneous velocities may be averaged, for example, by determining the mean, median, or similar, of the time series of the instantaneous velocities.

In some embodiments, the device 100 may be determined to be not immersed in a fluid such as a liquid (for example, water or any other liquid) when the first and second velocities (which may be the average first and second velocities, the time series of instantaneous first and second velocities, or the averaged time series of instantaneous first and second velocities) are equal or differ by less than a threshold. This may be, for example, when the first and second velocities are comparable in size or comparable in order. In some embodiments, the threshold may be at least 1% of the first or second velocity. In other embodiments, the threshold may be higher and may, for example, be at least 2%, at least 5%, or at least 10% of the first or second velocity. In some embodiments, the device 100 may be determined to be immersed in a fluid such as a liquid (for example, water or any other liquid) when the first and second velocities differ by more than the threshold. In a similar manner, in some embodiments, the device 100 may be determined to be immersed in a fluid such as a gas (for example, air or any other gas) when the first and second velocities are equal or differ by less than the threshold.

Although not illustrated, in another example embodiment, the comparison to determine whether the device 100 is immersed in a fluid may comprise a comparison of a first acceleration for the device 100 determined from the acceleration signal acquired by the accelerometer 102 and a second acceleration for the device 100 determined from the pressure within the device detected by the pressure sensor 104. In this example embodiment, the second acceleration may be determined from the detected pressure by performing a double differentiation of the detected pressure. The first and second accelerations may be instantaneous accelerations or average accelerations (for example, instantaneous accelerations averaged over a set time interval). The determination of whether the device 100 is immersed in a fluid may then be performed as described with reference to the other example embodiments, namely by comparing the difference between the first and second accelerations to a threshold.

Although not illustrated, in another example embodiment, the comparison to determine whether the device 100 is immersed in a fluid may comprise a comparison of the change in height for the device 100 determined from the acceleration signal acquired by the accelerometer 102 over a predefined time period with a change in height for the device 100 determined from the change in pressure detected by the pressure sensor 104 over the predefined time period. In this example embodiment, the change in height for the device 100 is determined from the change in pressure detected by the pressure sensor 104 by using Equation (3). The determination of whether the device 100 is immersed in a fluid may then be performed as described with reference to the other example embodiments, namely by comparing the difference between the change in height determined from the acceleration signal acquired by the accelerometer 102 and the change in height determined from the change in pressure detected by the pressure sensor 104 to a threshold. In some embodiments, the device 100 may be determined to be not immersed in a fluid such as a liquid (for example, water or any other liquid) when the difference is equal to or less than the threshold. In these embodiments, the threshold may be, for example, at least 10% or at least 20%. As the ratio between air and water is large.

Although not illustrated, in any of the embodiments disclosed herein, the method may further comprise confirming that the determination of whether the device 100 is immersed in a fluid is correct or reliable. For example, in some embodiments, this can be based on whether the change in the height determined from the acceleration signal acquired by the accelerometer 102 and the change in the pressure detected by the pressure sensor 104 are identical in sign (i.e. are both negative or both positive values). Where the height determined from the acceleration signal acquired by the accelerometer 102 and the change in the pressure detected by the pressure sensor 104 are identical in sign, the determination of whether the device 100 is immersed in a fluid is confirmed as correct. On the other hand, where the height determined from the acceleration signal acquired by the accelerometer 102 and the change in the pressure detected by the pressure sensor 104 are opposite in sign, the determination of whether the device 100 is immersed in a fluid is confirmed as incorrect. In this latter case, the method may be repeated from the start.

In another example of confirming the reliability of the determination of whether the device 100 is immersed in a fluid, the method may further comprise a determination as to whether the detected change in pressure is reliable. For example, this can comprise determining a ratio of the change in height of the device 100 to the time period over which the height change occurs to acquire a vertical velocity of the device 100 and comparing the acquired vertical velocity with a threshold to determine whether the detected change in pressure is reliable. The detected change in pressure is determined to be reliable where the acquired vertical velocity of the device 100 is a realistic value for a human to move (for example, a value of less than 10 $ms^{-1}$). Otherwise, the detected change in pressure is determined to be unreliable. Similarly, for the detected change in pressure to be determined to be reliable, the size of the height change may need to match normal movements for a human (for example, a value of less than 5 meters over 1 second). Otherwise, the detected change in pressure is determined to be unreliable. Where the detected change in pressure is determined to be unreliable, the method may be repeated from the start.

In any of the embodiments disclosed herein, where the device 100 is determined to be immersed in a fluid, the method may further comprise determining the depth of the device 100 below a surface of the fluid. When determining the depth of the device 100 below a fluid surface, the linear approximation in Equation (3) may be integrated to acquire the following for use in the depth determination:

$$P = P_0 e^{-\gamma(H-H_0)} \quad (4)$$

where $P_0$ is the pressure at a reference level (for example, typically, $P_0$ is equal to 1013 hPa at sea level) and $H_0$ is the height at the reference level (for example, typically, $H_0$ is equal to zero meters at sea level), the constant $$\gamma = \frac{M \cdot g}{R \cdot T},$$

where M is molecular mass, g is gravitational constant (which is equal to 9.81 ms$^{-2}$), R is universal gas constant, and T is temperature. As previously mentioned, the constant $\gamma$ is approximately 1000 times larger in water than it is in air. A similar equation can be derived for the acceleration.

In any of the embodiments disclosed herein where the device 100 comprises a valve 204, the method may further comprise allowing the valve 204 to open when the device 100 is determined to be not immersed in the fluid such as a liquid (for example, water or any other liquid) and prohibiting opening of the valve 204 when the device 100 is determined to be immersed in that fluid. In a similar manner, the method may comprise allowing the valve 204 to open when the device 100 is determined to be immersed in a fluid such as a gas (for example, air or any other gas). Thus, the valve 204 can be controlled to open or to remain closed. In other words, the valve 204 can be controlled to switch between an open state and a closed state. In any of the embodiments described herein, the determination of whether the device 100 is immersed in a fluid may be executed at any arbitrary time instant in order to decide whether to allow the valve 204 to open. It is noted that checking the reliability of the determination of whether the device 100 is immersed in a fluid (as described earlier) can prevent the valve 204 from opening while the device 100 is immersed in a fluid such as a liquid.

In some of these embodiments, where the valve 204 is allowed to open, the valve 204 may close once the pressure within the device 100 is equalised with a pressure outside the device 100. In other words, the valve 204 may only be allowed to remain open for a period of time that is long enough for the pressure to equalise, after which the valve 204 is closed again. For example, when the device 100 is in air, the outside pressure does not change by large amounts and continuous equalisation is not necessary. In some examples, the time period for which the valve 204 is allowed to remain open can be a time period of less than 1 second, less than 3 seconds, less than 5 seconds, less than 10 seconds, or less than 30 seconds. In some embodiments, the time period can be set based on the material of the flexible membrane that covers at least one aperture 204. For example, the time period may be set longer for a material that poses resistance to the pressure equalisation. In some embodiments, the time period may be proportional to (the product of) the resistance posed by the membrane and the capacity of the volume of the pressure chamber 108 or the device 100 in the absence of a pressure chamber.

The processor 106 of the device 100 may be configured to control the valve 204 in the manner described herein. In some embodiments, the valve 204 may initially be in a closed state (for example, the processor 106 of the device 100 may initially assume that the device 100 is immersed in a liquid) and then the valve 204 may be opened in the manner described herein. In this way, the vent 204 is only opened at the appropriate time (for example, when it is detected that the device 100 is immersed in a gas such as air) to ensure that the internal components of the device 100 are protected.

There is therefore provided an improved device and method for determining whether the device is immersed in a fluid.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention.

It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of

The invention claimed is:

1. A method for determining whether a device is immersed in a fluid, the method comprising:
   acquiring an acceleration signal for the device;
   detecting a pressure within the device;
   determining a change in height for the device from the acquired acceleration signal over a predefined time period;
   detecting a change in pressure from the pressure detected within the device over the predefined time period; and
   determining whether the device is immersed in a fluid based on a comparison of a first value determined based on the acquired acceleration signal with a second value determined based on the detected pressure,
   wherein the step of determining whether the device is immersed in the fluid is based on a comparison of the determined change in height with the detected change in pressure.

2. The method as claimed in claim 1, wherein determining whether the device is immersed in the fluid comprises:
   determining a ratio of the determined change in height to the detected change in pressure; and
   identifying the fluid in which the device is immersed based on the determined ratio.

3. The method as claimed in claim 1, wherein the method further comprises:
   determining a change in pressure from the change in height determined from the acquired acceleration signal; and
   wherein determining whether the device is immersed in the fluid is based on a comparison of the determined change in pressure with the detected change in pressure.

4. The method as claimed in claim 3, wherein:
   the device is determined to be not immersed in the fluid when the determined change in pressure and the detected change in pressure are equal or differ by less than a threshold; and
   the device is determined to be immersed in the fluid when the determined change in pressure and the detected change in pressure differ by more than the threshold.

5. The method as claimed in claim 1, the method further comprising:
   determining a first velocity of the device based on the determined change in height over the predefined time period;
   determining a second velocity of the device based on the detected change in pressure over the predefined time period; and
   wherein determining whether the device is immersed in the fluid is based on a comparison of the determined first velocity with the determined second velocity.

6. The method as claimed in claim 1, the method further comprising:
   determining a ratio of the change in height to the time period over which the height change occurs to acquire a vertical velocity of the device; and
   comparing the acquired vertical velocity with a threshold to determine whether the detected change in pressure is reliable.

7. The method as claimed in claim 1, the method further comprising allowing a valve of the device to open when the device is determined to be not immersed in the fluid and prohibiting opening of the valve when the device is determined to be immersed in the fluid.

8. The method as claimed in claim 7, the method further comprising closing the valve once the pressure within the device is equalized with a pressure outside the device.

9. A computer program product comprising a non-transitory computer readable medium, the computer readable medium having computer readable code embodied therein, the computer readable code being configured such that, on execution by a suitable computer or processor, the computer or processor is caused to perform the method of claim 1.

10. A device comprising:
    an accelerometer configured to acquire an acceleration signal for the device;
    a pressure sensor configured to detect a pressure within the device; and
    a processor configured to determine whether the device is immersed in the fluid based on a comparison of a first value determined based on the acquired acceleration signal with a second value determined based on the detected pressure,
    wherein the processor is further configured to:
      determine a change in height for the device from the acquired acceleration signal over a predefined time period;
      detect a change in pressure from the pressure detected within the device over the predefined time period; and
      determine whether the device is immersed in the fluid is based on a comparison of the determined change in height with the detected change in pressure.

11. The device as claimed in claim 10, the device further comprising a pressure chamber housing the pressure sensor, wherein the pressure chamber has a volume that is less than a maximum volume.

12. The device as claimed in claim 10, the device further comprising
    a valve to allow fluid to enter the device when the valve is open,
    wherein the processor is configured to:
      allow the valve to open when the device is determined to be not immersed in the fluid; and
      prohibit opening of the valve when the device is determined to be immersed in the fluid.

13. The device as claimed in claim 10, the device further comprising one or more apertures, wherein the one or more apertures are covered by a flexible and impermeable membrane.

14. The device as claimed in claim 13, wherein the pressure sensor is positioned less than a maximum distance from at least one of the one or more other apertures.

15. A method for determining whether a device is immersed in a fluid, the method comprising:
    acquiring an acceleration signal for the device;
    detecting a pressure within the device; and
    determining whether the device is immersed in a fluid based on a comparison of a first value determined based on the acquired acceleration signal with a second value determined based on the detected pressure,
    wherein the first value and the second value have a common unit of measurement.

16. The method of claim 15, wherein the common unit of measurement is pressure.

17. The method of claim 16, further comprising:
determining a change of height of the device based on the acceleration signal,
determining a change of determined pressure as the first value based on the change of height, and
determining a change of detected pressure as the second value based on the detected pressure.

18. The method of claim 15, wherein the common unit of measurement is one of velocity or acceleration.

19. The method of claim 18, further comprising:
determining a detected one of velocity or acceleration of the device as the first value based on the acceleration signal,
determining a determined change of height over time based on changes in the detected pressure over time, and
determining a determined one of velocity or acceleration as the second value based on the determined change of height.

20. A non-transitory computer readable medium comprising program code that, when executed by a processing system, causes the processing system to perform the method of claim 15.

* * * * *